(12) United States Patent
Nekhendzy et al.

(10) Patent No.: US 6,567,702 B1
(45) Date of Patent: May 20, 2003

(54) ELICITING ANALGESIA BY TRANSCRANIAL ELECTRICAL STIMULATION

(75) Inventors: Vladimir Nekhendzy, Palo Alto, CA (US); Mervyn Maze, London (GB)

(73) Assignee: The Board of Trustees of the Leland Stanford Junior University

( * ) Notice: Subject to any disclaimer, the term of this patent is extended or adjusted under 35 U.S.C. 154(b) by 269 days.

(21) Appl. No.: 09/687,985

(22) Filed: Oct. 13, 2000

Related U.S. Application Data

(60) Provisional application No. 60/159,784, filed on Oct. 15, 1999.

(51) Int. Cl.[7] ................................................. A61N 1/34
(52) U.S. Cl. ........................... 607/46; 607/66; 607/68; 607/70; 607/139; 607/72; 607/140
(58) Field of Search ...................... 607/66, 68, 70–74, 607/139–141, 46–47

(56) References Cited

U.S. PATENT DOCUMENTS

| | | | |
|---|---|---|---|
| 3,513,851 A | 5/1970 | Smith et al. ................. | 128/422 |
| 3,835,833 A | 9/1974 | Limoge ....................... | 128/1 C |
| 3,955,583 A | 5/1976 | Horauf .................... | 128/420 R |
| 3,989,051 A | 11/1976 | Nozhnikov et al. .......... | 128/421 |
| 4,121,593 A | 10/1978 | Kastrubin et al. ........... | 128/421 |
| 4,140,133 A | 2/1979 | Kastrubin et al. ........... | 128/421 |
| 4,185,640 A | 1/1980 | Kastrubin et al. ........... | 128/421 |
| 4,334,525 A | 6/1982 | Kastrubin .................... | 128/1 C |
| 4,383,522 A | 5/1983 | Kastrubin et al. ........... | 128/1 C |
| 4,541,432 A * | 9/1985 | Molina-Negro et al. ....... | 607/46 |
| 4,646,744 A | 3/1987 | Capel ...................... | 128/423 R |
| 4,724,841 A | 2/1988 | Kastrubin et al. ....... | 128/420 R |
| 4,844,075 A | 7/1989 | Liss et al. ................ | 128/419 R |
| 4,856,526 A | 8/1989 | Liss et al. .................... | 128/422 |
| 5,084,007 A | 1/1992 | Malin et al. ................... | 604/20 |
| 5,163,444 A | 11/1992 | Braverman .................. | 128/783 |
| 5,332,401 A * | 7/1994 | Davey et al. ............... | 607/116 |
| 5,342,410 A | 8/1994 | Braverman .................. | 607/58 |
| 5,387,231 A | 2/1995 | Sporer .......................... | 607/48 |
| 5,571,149 A | 11/1996 | Liss et al. ..................... | 607/72 |
| 5,593,432 A | 1/1997 | Crowther et al. ............. | 607/46 |
| 5,776,170 A | 7/1998 | MacDonald et al. .......... | 607/46 |
| 5,851,223 A | 12/1998 | Liss et al. ..................... | 607/46 |

FOREIGN PATENT DOCUMENTS

| | | | |
|---|---|---|---|
| SU | 1074543 | * | 11/1983 |
| SU | 1389780 | * | 12/1987 |
| SU | 1489719 | | 3/1989 |
| SU | 1507404 | | 5/1989 |
| SU | 1522500 | * | 7/1989 |

* cited by examiner

*Primary Examiner*—Teresa Walberg
*Assistant Examiner*—Shawntina Fuqua
(74) *Attorney, Agent, or Firm*—Lumen Intellectual Property Services, Inc.

(57) ABSTRACT

A method of eliciting analgesia in a human subject by Transcranial Electrical Stimulation (TCES) is provided. Electrodes are secured to the skin of the subject's head and used to apply an electrical current to the electrodes. The current includes a direct current combined with rectangular current pulses (alternating current) delivered at a frequency of between 30 and 65 Hz. The frequency at which the pulses are delivered is periodically changed to a different value within the 30–65 Hz range. The total current supplied, a sum of the DC component and a Mean Absolute Deviation (MAD) of the current pulses, preferably has a value between 0.2 and 20 mA. The method is used during surgery and the post-operative procedure, and may also be used to treat a wide variety of neurological and other conditions.

23 Claims, 11 Drawing Sheets

ELICITING ANALGESIA BY
TRANSCRANIAL ELECTRICAL
STIMULATION

CROSS-REFERENCE TO RELATED APPLICATIONS

This application claims the benefit of U.S. Provisional Application No. 60/159,784 filed Oct. 15, 1999, which is herein incorporated by reference.

STATEMENT REGARDING FEDERALLY SPONSORED RESEARCH OR DEVELOPMENT

This invention was made with Government support under contract GM30232 awarded by the National Institutes of Health (NIH). The Government has certain rights in this invention.

FIELD OF THE INVENTION

This invention relates generally to generating analgesic effects by Transcranial Electrical Stimulation (TCES). More particularly, it relates to specific operating conditions for TCES and a method for using animal models to determine the optimal operating conditions.

BACKGROUND ART

The use of electrical currents for the purpose of producing narcosis or analgesia was pioneered by the French physiologist Leduc nearly 100 years ago. Over the next 70 years, several attempts were made to produce and maintain a state of general anesthesia by administering different parameters of electrical currents, applied to the skin of the subject's head (i.e., transcranially and transcutaneously). However, due to the high intensity of current required to induce general anesthesia, these efforts were abandoned and superseded by attempts to produce analgesia, rather than general anesthesia, by application of electrical currents. Different types of Transcranial Electrical Stimulation (TCES) are suggested in the literature under a wide variety of names, including Cranial Electrotherapy Stimulation (CES), Low Current Electrostimulation, Auricular Microstimulation, and others [Limoge, 1999]. However, only French [Limoge, 1975] and Russian [Lebedev, 1988] currents are thought to produce an analgesic effect powerful enough to be utilized in clinical anesthesiology. Limoge currents consist of high frequency (166 kHz) intermittent bursts of bidirectionally balanced current "packed" into trains. The current is applied transcranially and transcutaneously at 100 Hz for 4 msec at 6 msec intervals. These currents are described in part in U.S. Pat. No. 3,835,833, issued to Limoge. TCES with Limoge currents is applied through a frontal cathode and a pair of anodes located at the level of mastoid bones [Mantz, 1992]. TCES with Limoge current has been successfully used as part of an anesthetic management in a wide variety of surgical cases. It has been shown to:

increase the potency of nitrous oxide in humans by 30–40% [Stanley, 1982A];

reduce the need for opiates during neuroleptanesthesia by 50–80% [Stanley, 1982B];

potentiate opioid-induced analgesia in rats [Dougherty, 1989]; and decrease minimum alveolar concentration (MAC) of halothane in rats [Mantz, 1992].

In the mid-1980's, Russian investigators at the Pavlov Institute of Physiology in St. Petersburg determined parameters of TCES that produce a more profound analgesic effect than that observed with TCES with Limoge currents [Lebedev, 1983, 1988A, 1988B; Kovalev, 1987]. The major difference from Limoge currents was the use of a combination (2:1 or 3:1 ratio) of direct (DC) and alternating current (AC) of lower frequency (77–78Hz). The resultant current is also applied through frontal cathode and retromastoid anodes. The analgesic effect of "Lebedev current" was thought to be mediated by the AC, while the DC potentiated its action and eliminated the inherent seizure-provoking properties of AC [Rychkova, 1994]. This method of TCES has been successfully used in Russia in thousands of patients for different types of surgery, including cardiothoracic procedures, and in different age groups, including pediatrics [Katsnelson, 1987, 1989; Kartavkin, 1987; Zamiatnina, 1987]. So profound was the analgesic effect of TCES suggested by Russian researchers that intraoperative use of opioid narcotics in some cases could be completely avoided, and the analgesic effect extended into the immediate postoperative period [Lebedev, 1989]. This method has also been used successfully for treatment of chronic pain syndromes in awake subjects [Skorometz, 1987; Akimov, 1987; Gurchin, 1987; Kasimova, 1987]. Recently, Lebedev has restricted TCES stimulating parameters to administration of AC only, citing the same analgesic effect as with the combination of DC and AC [Lebedev, 1998]; however, no experimental data has been published to support that claim.

TCES with either Limoge or Lebedev current facilitates rapid recovery from general anesthesia without side effects such as respiratory depression, nausea and vomiting, itching, urinary retention, and immunosuppression [Stinus, 1990; Katsnelson, 1987]. Furthermore, both TCES modalities have been used successfully in the management of alcohol and opiate withdrawal states in awake patients [Auricombe, 1990; Krupitski, 1991]. Lebedev current has also been shown to promote tissue repair and decrease the incidence of surgical wound infections [Lebedev, 1998].

Despite these encouraging results, good controlled clinical studies are lacking. In addition, TCES studies in rats either failed to document prolongation of tail flick latency (TFL) with Limoge current [Stinus, 1990], or TFL responses were not studied [Lebedev, 1988]. TFL test is a standard measure of analgesia production in rats and mice, and correlates well with analgesic potency of drugs in humans. Lack of good controlled studies and consensus among researchers on the "best" TCES stimulation parameters has contributed to the conflicting results between laboratories regarding the efficacy of TCES and the TCES mechanism of action [Alling, 1990]. Broad disagreement exists about optimal current intensity, electrode positioning and configuration, signal waveform, and frequency. However, it has been established that frequency is the most important variable in determining efficacy of analgesia production. It is also agreed that a tolerance effect may be established relatively rapidly: after a short time period, analgesic effects are no longer observed. In order to re-establish analgesia, the signal must be adjusted periodically.

Various researchers have developed different signal parameters for TCES. A series of U.S. patents have been issued to Kastrubin et al. and Nozhnikov et al., including U.S. Pat. Nos. 3,989,051; 4,121,593; 4,140,133; 4,185,640; 4,334,525; 4,383,522; and 4,724,841. Their devices, generally used for electroanesthesia, generate square pulses of varied current, duration, and frequency. Recommended frequencies are above 100 Hz, and stimulation is by a combination of direct and alternating current. The combination of AC and DC is also included in an electrotherapy method disclosed in U.S. Pat. No. 5,387,231, issued to Sporer. This method is primarily for pain relief through muscle relaxation and uses frequencies typically below 15 Hz and microampere current value that is much lower than typically used in TCES.

Other TCES parameters have been used for a variety of different applications. For example, currents somewhat similar to Limoge currents are employed for treating headaches, as described in U.S. Pat. Nos. 4,844,075 and 4,856,526, both issued to Liss et al. Other methods involve applying trains of pulsed current separated by off periods, as described in U.S. Pat. No. 4,646,744, issued to Capel, or trains of different frequencies, U.S. Pat. No. 5,593,432, issued to Crowther et al., in order to avoid acclimation of the nerves to the imposed signal. Both of these methods are directed toward drug addiction recovery.

Mechanism of TCES action remains unknown. Perhaps the most plausible explanation is that the electrical current causes depolarization of nerve terminals with the release of inhibitory neurotransmitter(s), interrupting nociceptive (pain receptor-related) processing. The identity of mediating neurotransmitter(s) and nociceptive pathway(s) involved has been widely debated; opioids, serotonin, and norepinephrine have each been implicated as a possible mechanism for the analgesic response to TCES [Airapetov, 1987; Lebedev, 19988A; Malin, 1989; Mantz, 1992].

Thorough studies are needed both to better understand the mechanism of TCES and to correctly determine the optimal operating conditions. Absent a neurobiologic substrate to explain observed analgesia, mainstream medical opinion remains skeptical, and TCES continues to be more of a curiosity than an established clinical practice outside of certain centers in France and Russia.

OBJECTS AND ADVANTAGES

Accordingly, it is a primary object of the present invention to provide an improved Transcranial Electrical Stimulation (TCES) method employing optimal parameters that are not used in prior art methods.

It is a further object of the invention to provide a TCES method using parameters obtained from novel experimental studies. For the first time, electrode application in animal (rat) studies, from which optimal parameters are obtained, mimics electrode application in humans during clinical practice.

It is an additional object of the invention to provide a TCES method using parameters obtained from experimental studies that indicate that the mechanism of analgesia production may involve cutaneous nerve activation.

It is another object of the present invention to provide a TCES method using parameters obtained from randomized, blinded studies using accepted measures of analgesia production in rats.

SUMMARY

These objects and advantages are attained by a method of eliciting analgesia in a human subject using Transcranial Electrical Stimulation (TCES) with novel operating parameters. The method is intended primarily for use during surgery or in the post-operative state, but is also useful for treating a wide variety of medical conditions, including chronic pain syndrome, alcohol withdrawal, opiate withdrawal, Attention Deficit Disorder, anxiety, depression, mood disturbance, Post-Traumatic Stress Disorder, immune system depression, decreased would healing, Parkinson's disease, Alzheimer's disease, neurological dysfunction, appetite disturbance, and sexual dysfunction. It can also be used to generate desired effects such as elevated mood and stimulated immune system. The present invention differs from prior art TCES in its use of parameters derived from animal studies that more closely mimic TCES application in humans, and are therefore more likely to duplicate the mechanism responsible for generating analgesia in humans.

The method is performed by removably fixing a first electrode and a pair of second electrodes to the skin of the subject's head and delivering an electrical current to the electrodes. The current consists of a direct current (DC) component and rectangular current pulses supplied at a particular frequency within an effective range of 30–65 Hz. Preferably, the particular frequency is within a range of 40–60 Hz, and most preferably approximately 60 Hz. However, the optimal frequency depends on the particular human subject. At periodic intervals of 5–60 minutes, the frequency is changed to a different frequency within the effective range. Preferably, the frequency is also changed to a value outside of the effective range, but within 10–100 Hz, at longer intervals such as 15–60 minutes.

While frequency is believed to be the most important parameter for determining efficacy of analgesia production, other parameters are also important. The total current supplied, a sum of the DC component and a Mean Absolute Deviation (MAD) of the current pulses, preferably has a value between 0.2 and 20 mA, and most preferably between 2 and 10 mA. Preferably, the ratio between the value of the DC component and the MAD value of the alternating current is between 5:1 and 1:1, and most preferably approximately 2:1. Each AC pulse preferably has a duration of below approximately 8 msec, and most preferably of approximately 3.5 msec. The polarity of the current supplied can be switched at regular intervals such as 5–15 minutes.

DETAILED DESCRIPTION

Figure 1:
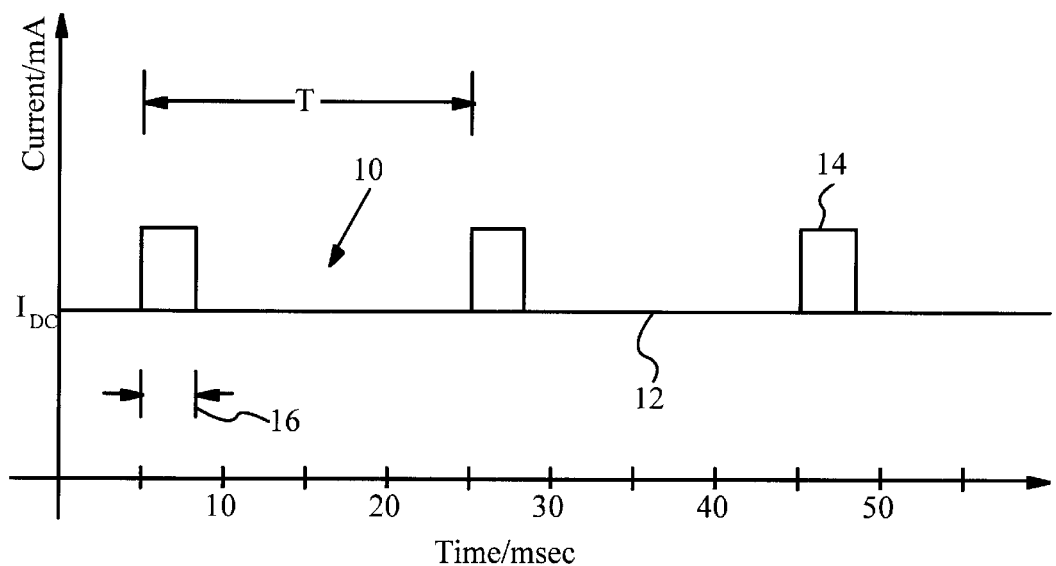
FIG. 1 is a diagram of a preferred waveform for delivering TCES according to the method of the present invention.

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

The present invention provides a method for applying electrical current transcranially to a human patient in order to affect the patient's nervous system. Current is applied through electrodes secured to the skin of a patient's head, through a single cathode at the forehead and paired anodes near the upper part of the neck, e.g., at the level of the mastoid processes. Specifically, the applied current elicits analgesia in the patient and may be used as part of anesthesia management for surgical procedures performed under general anesthesia, during the post-operative period, and for non-pharmacological treatment of acute and chronic pain. Additional effects such as stimulated immune system and improved wound healing enhance the method's usefulness during the post-operative period; in fact, the method may be used for these effects alone and not for pain treatment. Other applications are discussed below. The method is a variation of Transcranial Electrical Stimulation (TCES) and uses frequency parameters that have not been recommended previously. Frequency is widely believed to be the most important parameter in determining analgesic effect. For the first time in studies in rats, cutaneous electrode positioning was employed mimicking the one used in clinical practice. These studies are therefore much more likely to duplicate the mechanism actually responsible for analgesic effects in humans, a fact emphasized by the experimental data discussed below, which shows that the elicited analgesic effect appears to be blocked by local anesthetic injected under electrode sites. The elicited analgesic effect was substantial.

Also provided is a novel method for applying stimulating TCES electrodes to live rats cutaneously (i.e., on the skin surface), rather than the standard practice of subcutaneous or cranial bone application of electrodes.

The techniques of the present invention can be implemented using a controllable waveform generator and suitable electrodes positioned at the forehead and at the upper part of the neck e.g., below the mastoid processes. The hardware preferably includes conventional state-of-the-art components and circuitry. It will be apparent to one of average skill in the art, upon reading this disclosure, how to select and program suitable hardware. Application of current to a patient may range from minutes to days, depending on the condition being treated or desired results. It may also follow a schedule in which the patient is treated for a predetermined period of time over successive days. Because the primary distinguishing features of the present invention relate to the specific TCES application parameters, the following description will focus on these parameters.

The present method uses many of the parameters derived by Lebedev et al., but differs in the frequencies employed and the manner in which these frequencies are applied. FIG. 1 shows a preferred embodiment of a TCES waveform 10 of the present invention as a plot of current versus time. Many of the parameters characterizing waveform 10 may be controlled independently. All of the numerical values used within this description are approximate values. Values are considered to be approximately equal if they are within 1% of each other.

Waveform 10 is a combination of direct current (DC) 12 and alternating current (AC) 14, which is in rectangular pulses. Rectangular current pulses begin at the current level of DC, $I_{DC}$. $I_{AC}$ is calculated as a Mean Absolute Deviation (MAD) value (also called an AC average) of the time-varying AC component; the peak-to-peak current value of pulses 14 is larger than $I_{AC}$. Preferably, the ratio of $I_{DC}$ to $I_{AC}$ is 2:1, but it may also be any value between 5:1 and 1:1. For example, if the ratio of $I_{DC}$ to $I_{AC}$ is 2:1 for a total current of 3 mA, $I_{DC}$ is 2 mA and $I_{AC}$ is 1 mA. It has been proposed that direct current reduces skin impedance, thereby allowing the AC current to penetrate the skin. The total current delivered is preferably between 0.2 and 20 mA, and most preferably between 2 and 10 mA.

To prevent the occurrence of DC skin burns, the polarity of the applied current is changed at regular intervals, for example, every 5–10 minutes. The resultant waveform is simply a reflection of waveform 10 about the time axis.

The pulse frequency is defined as 1/T, with T as shown in FIG. 1. The pulse frequency used in the present invention is substantially different from that of the prior art. Rather than a single frequency, the present invention uses a range of optimal frequencies that are quite different from the frequencies recommended in the prior art. For example, Lebedev indicates a single frequency between 77 and 78 Hz.

For the present invention, the effective range of frequencies is between 30 and 65 Hz, with frequencies between 40 and 60 Hz possibly being preferred (optimal). Examination of the Biphasic Sigmoid $E_{max}$ model fit for the Tail Flick Latency and the Hot Plate tests (FIGS. 3C and 3D, described below), derived from a population pharmacodynamic analysis, indicates that there is a range of "best" frequencies (40–60 Hz), with 60 Hz possibly being the single "best" by the results of both tests pooled together. During TCES current application, a certain pulse frequency within the preferred or effective range can be maintained, or delivered frequencies can be periodically scanned within the preferred and effective ranges. Frequency scanning should not only increase the efficacy of analgesic effect, but also help to counteract a tolerance-induced decrease in the analgesic effect (described above), should that occur. Preferably, the frequency is maintained at a particular value within the effective range for a relatively short time period such as 5–60 minutes, and then switched to a different frequency value within the effective range and held at this different value for a comparable time period.

At preset intervals, the pulse frequency may also be changed to a value between 10 Hz and 100 Hz. While the preferred frequency range, 40–60 Hz, should provide the best analgesic effect, it is possible that some patients may not respond to this frequency. By periodically scanning frequencies outside of the preferred and effective ranges, a larger percentage of patients may be affected. Scanning outside the effective range preferably occurs at longer time intervals than does scanning within the effective range. For example, the frequency can be changed to a value within 10–100 Hz, but outside the effective range, at time intervals of between 15 and 60 minutes. The frequency is held at this value for a short time period such as 5–15 minutes before being returned to a value within the effective range.

As the frequency is changed, pulse duration 16 remains constant, so that only the time between pulses is shortened or extended. Preferably, the pulse duration 16 is held constant at a value of up to about 8 msec, even when pulse frequency changes. Most preferably, pulse duration 16 is approximately 3.5 msec.

In general, the optimal frequency value for eliciting analgesia depends on the particular person to whom the TCES current is being applied. This value can be determined empirically before an extended course of TCES is initiated or before surgery. The optimal value depends upon the sensitivity and requirements of the individual, and is therefore difficult to determine without at least some amount of experimentation.

Figure 2:
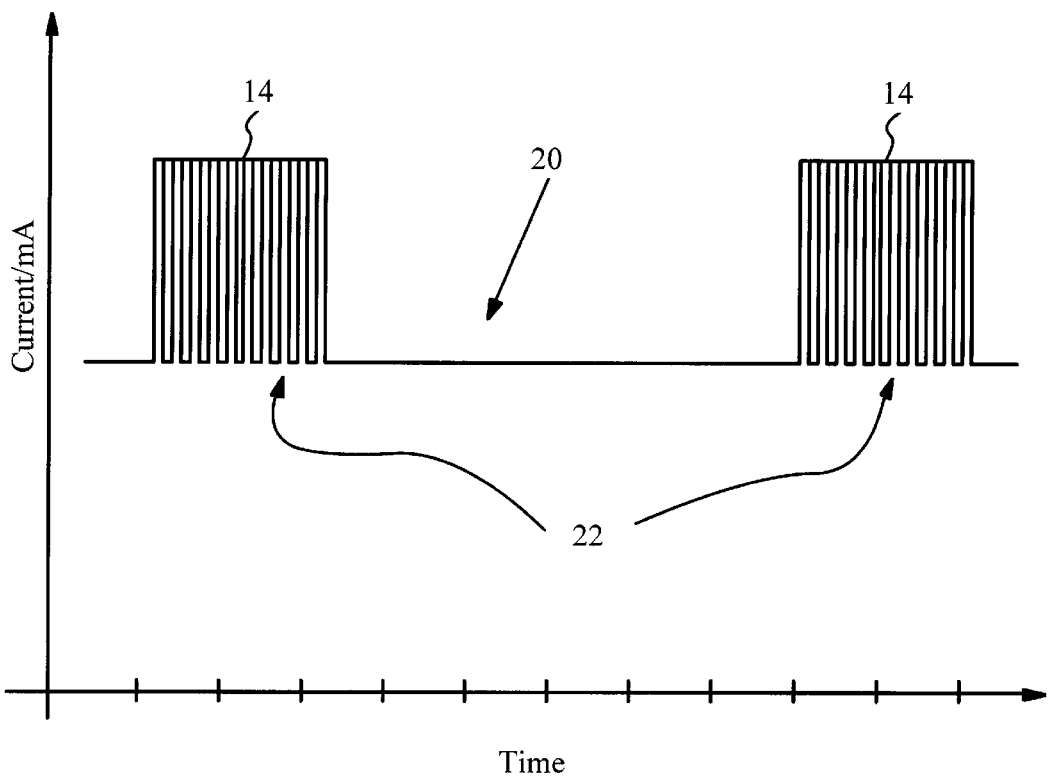
FIG. 2 is a diagram of an alternative waveform for delivering TCES.

Alternatively, instead of single pulses, the AC component of a TCES current may consist of wave trains, as shown in waveform 20 of FIG. 2 (not to scale). Each wave train 22 consists of individual high frequency pulses delivered at between 10 kHz and 10 MHz. Individual wave trains 22 are separated by DC current, and, again, are delivered at the preferred and effective frequencies in a manner described above. That is, during TCES current application, trains are delivered at a certain fixed frequency within the preferred or effective range, or delivered frequencies can be periodically scanned within the preferred and effective ranges. Again, at preset intervals, the train frequency can also be changed to a value between 10 and 100 Hz. In some cases, it may be preferable to apply only AC current, thereby avoiding the superficial skin burns caused by DC current application. AC current alone is supplied using the same parameters as detailed above for the combined current. While the animal studies described below indicate that AC current alone is not effective in eliciting analgesia, the effect in humans may be different. Further clinical studies in humans are needed to determine whether AC current would indeed be beneficial.

The preferred and effective frequency ranges of the present invention were determined through a set of novel experiments. These experiments represent the first use of cutaneous electrode placement in live rat models, a placement that mimics electrode placement during clinical application of TCES to humans. Experiments followed a randomized, controlled, blinded paradigm to assess analgesia in awake rats by using Tail Flick Latency (TFL) and Hot Plate (HP) tests. TFL test is believed to assess predominantly spinal mechanisms of analgesia, and prolongation of TFL has been shown to correlate well with the analgesic potency of drugs in humans [Grumbach, 1966]. HP test assesses a much more complex behavioral response, involving further processing of painful information from the spinal cord to the supraspinal level.

The Tail Flick Latency test is conducted by applying a painful stimulus to a rat's tail, usually heat in the form of a light beam, and measuring the time before the rat flicks its tail (the tail flick latency). Under TCES application, if the rat does not respond within a predetermined cut-off time, the stimulus is removed to prevent injury to the rat's tail. A baseline TFL, without application of TCES, is first determined; baseline TFL is usually between 2.5 and 3.5 seconds. The effect of TCES, manifested as a prolongation of TFL, is expressed as a percent of maximum possible effect (% MPE), defined as $$\% \; MPE = \frac{TFL_{TCES} - TFL_{baseline}}{TFL_{cut\text{-}off} - TFL_{baseline}} \times 100.$$

HP tests are similar in nature. A rat is placed on a preheated plate that is enclosed in a clear plastic box. The time for the rat to either jump up or lick its hind paw is recorded. Again, a baseline value is first measured, and a cut-off time (usually 60 seconds) is determined. % MPE is calculated as for TFL.

Figure 3A:
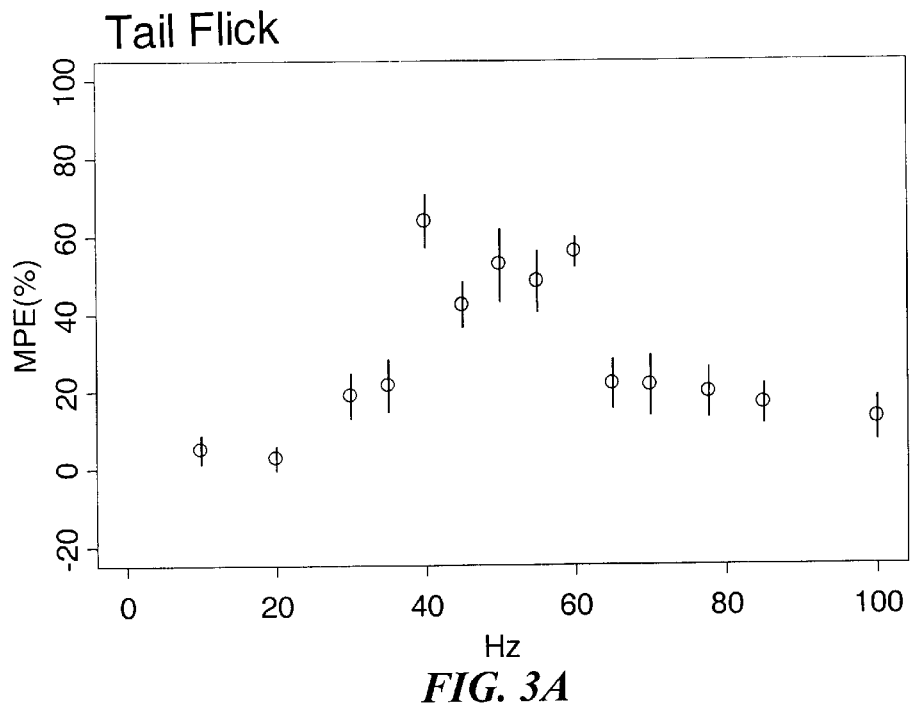
FIG. 3A is a graph of mean and standard error of % MPE at different TCES frequencies in the Tail Flick Latency test.
Figure 3B:
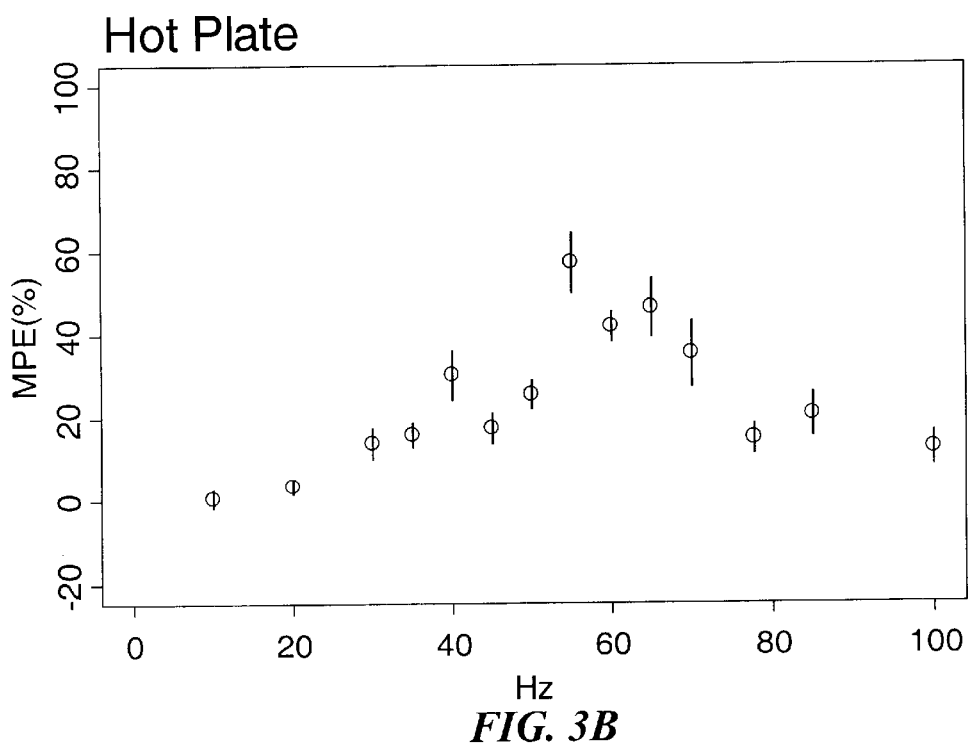
FIG. 3B is a graph of mean and standard error of % MPE at different TCES frequencies in the Hot Plate test.

FIGS. 3A and 3B are graphs showing the relationship between frequency in Hz and observed effect in % MPE in the TFL and HP tests, respectively. Open circles are mean values, while vertical lines represent standard errors. In the TFL tests, the observed mean effect increases between 30 and 60 Hz, with a steep drop in the mean effect occurring at higher frequencies. In the HP tests, the observed mean effect increases between 40 and 65 Hz, with a steep drop in the mean effect occurring at frequencies above 65 Hz.

Figure 3C:
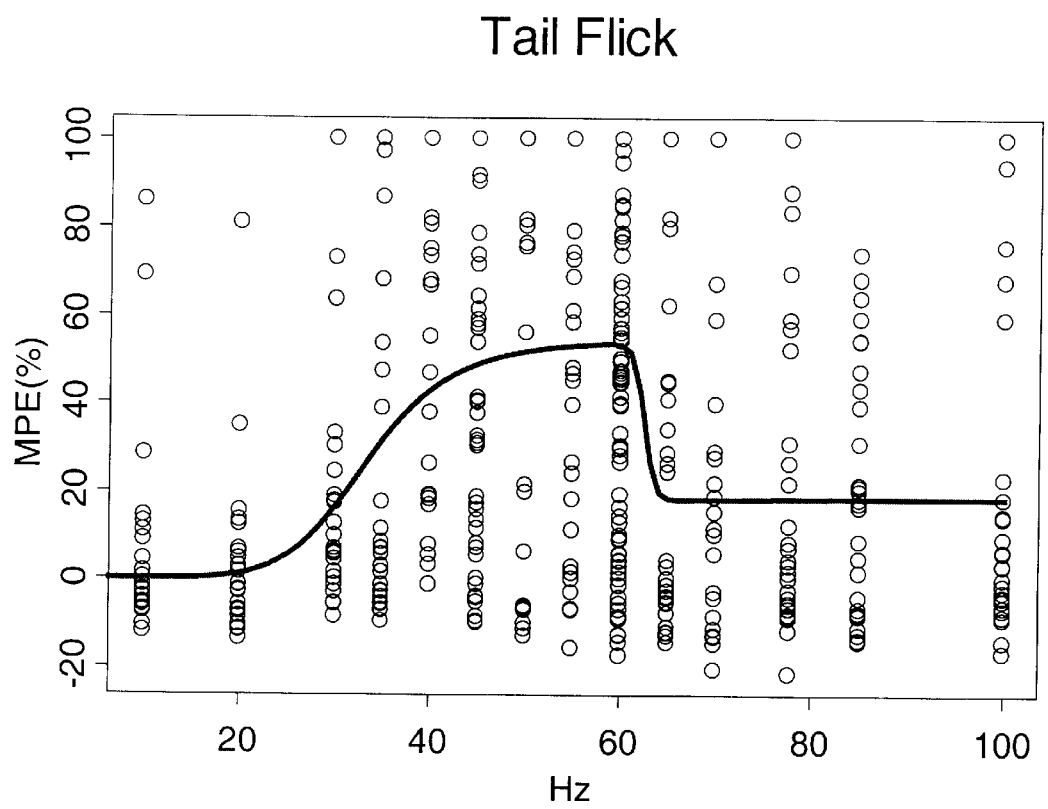
FIG. 3C is a graph of a Biphasic Sigmoid $E_{max}$ a model fit in the Tail Flick Latency test.
Figure 3D:
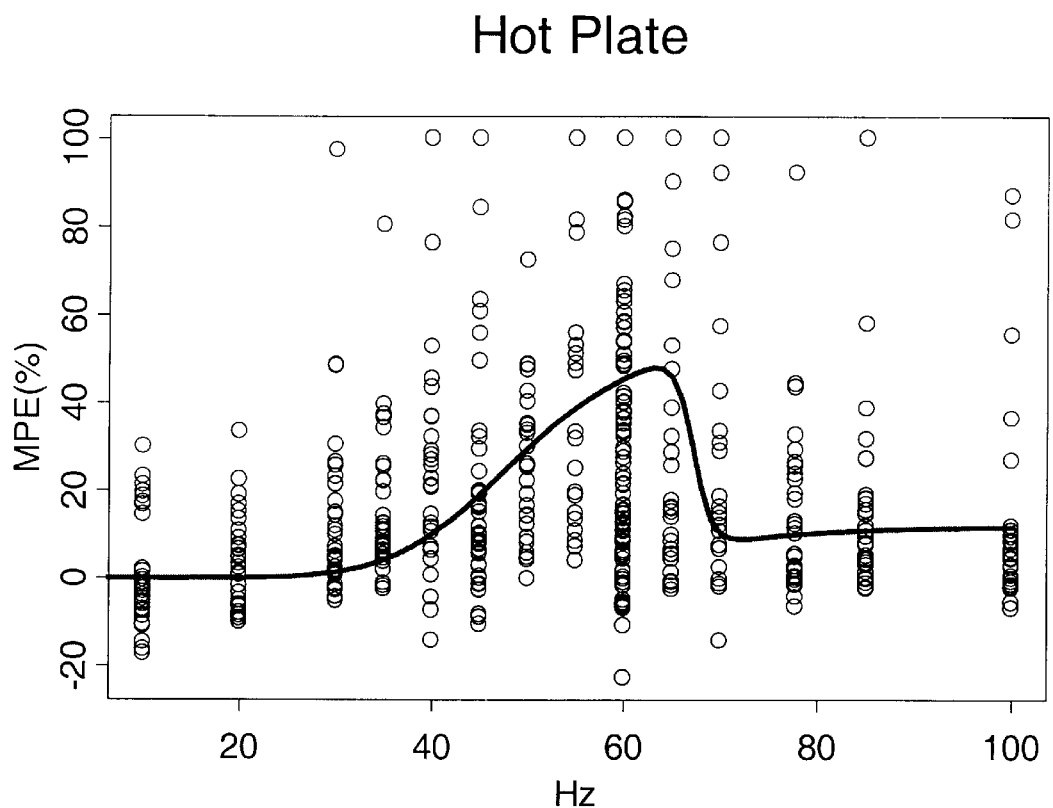
FIG. 3D is a graph of a Biphasic Sigmoid $E_{max}$ model fit in the Hot Plate test.

FIGS. 3C and 3D are graphs showing the experimental and predicted relationship between frequency in Hz and observed effect in % MPE in the Tail Flick Latency and Hot Plate tests, respectively. In these plots, open circles are individual data points, and the curve is a biphasic sigmoid $E_{max}$ model fit representing a typical rat. The model fit was derived from a population pharmacodynamic analysis using a mixed effects population model with NONMEM. Biphasic nonlinear $E_{max}$ and sigmoid $E_{max}$ models were considered. The best model was found to be a biphasic sigmoid $E_{max}$ model according to the following equation:

$$MPE = \frac{MPEa_{\max} Hz^{Na}}{Hza_{50}^{Na} + Hz^{Na}} - \frac{MPEb_{\max} Hz^{Nb}}{Hzb_{50}^{Nb} + Hz^{Nb}}.$$

Considering this equation to be the difference of an equation [a] represented by the first term and an equation [b] represented by the second term, the variables are as follows: MPE is the observed effect, $MPEa_{max}$ is the maximum observable effect for equation [a], $MPEb_{max}$ is the maximum observable effect for equation [b], Hz is the administered frequency in Hz, Na is the slope of the curve for equation [a], Nb is the slope of the curve for equation [b], $Hza_{50}$ is the frequency yielding half of the maximum observable effect for equation [a], and $Hzb_{50}$ is the frequency yielding half of the maximum observable effect for equation [b].

In the model, the intra-individual error was described with the following equation:

$$MPEm_j = MPEp_j(1 + \epsilon_j),$$

where $MPEm_j$ is the $j^{th}$ measured observation, $MPEp_j$ is the $j^{th}$ predicted observation by the model, and $\epsilon_j$ is the residual or intra-individual error of the $j^{th}$ observation. $\epsilon_j$ is a random quantity that is normally distributed with mean zero and unknown variance $\sigma^2$. The inter-individual error was modeled with a log-normal variance model:

$$P_i = TV\theta \exp(\eta_i),$$

where $P_i$ is the pharmacodynamic parameter of rat i, $TV\theta$ is the typical value of that population parameter, and $\eta_i$ is a random variable with mean zero and variance $\omega^2$. Parameter values were estimated with the first order estimation approach.

The derived model parameters are shown in Table 1 below:

TABLE 1

| Parameter | Typical Value | $\omega^2$ | Typical Value | $\omega^2$ |
|---|---|---|---|---|
| | Hot Plate | | Tail Flick | |
| MPEa$_{max}$ | 56.5 | NA | 54.4 | NA |
| MPEb$_{max}$ | 44.5 | NA | 36 | NA |
| Na | 7.25 | 2.66 | 7.45 | 3.63 |
| Nb | 70.1 | 6.87 | 119 | 1840.00 |
| Hza50 | 49.3 | 0.01 | 33.5 | 0.02 |
| Hzb50 | 67.2 | 0.02 | 62.4 | 0.08 |

Similarity of parameters between the Tail Flick Latency and Hot Plate tests indicates that the observed effect is reproducible using different experimental methodologies.

Analysis of the biphasic sigmoid $E_{max}$ model fit (FIGS. 3C and 3D), which models a response of a typical rat, indicates that the analgesic effect increases gradually between 30 and 60 Hz in the tail flick latency test and between 40 and 65 Hz in the hot plate test, with a steep drop in effect occurring at higher frequencies. A more close analysis of FIGS. 3C and 3D, considering the results of both types of experiments, indicates that 60 Hz may be the optimal frequency. While 60 Hz may be optimal for some patients, in general, a range of frequencies is recommended.

Figure 4A:
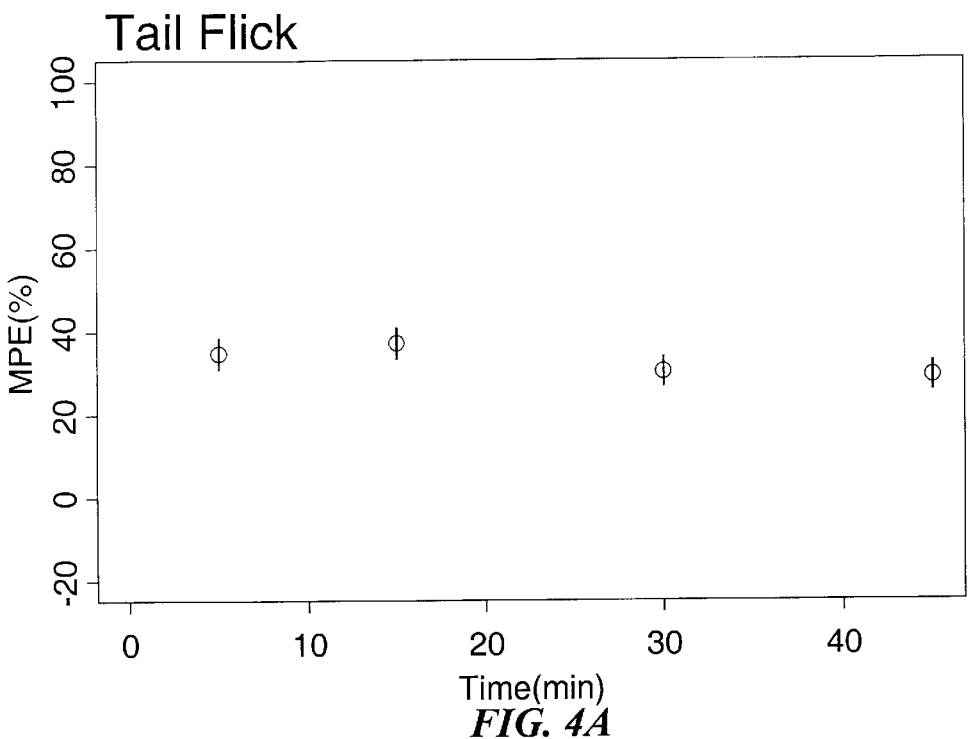
FIG. 4A is a graph of mean and standard error of % MPE at different times for all TCES frequencies in the Tail Flick Latency test.
Figure 4B:
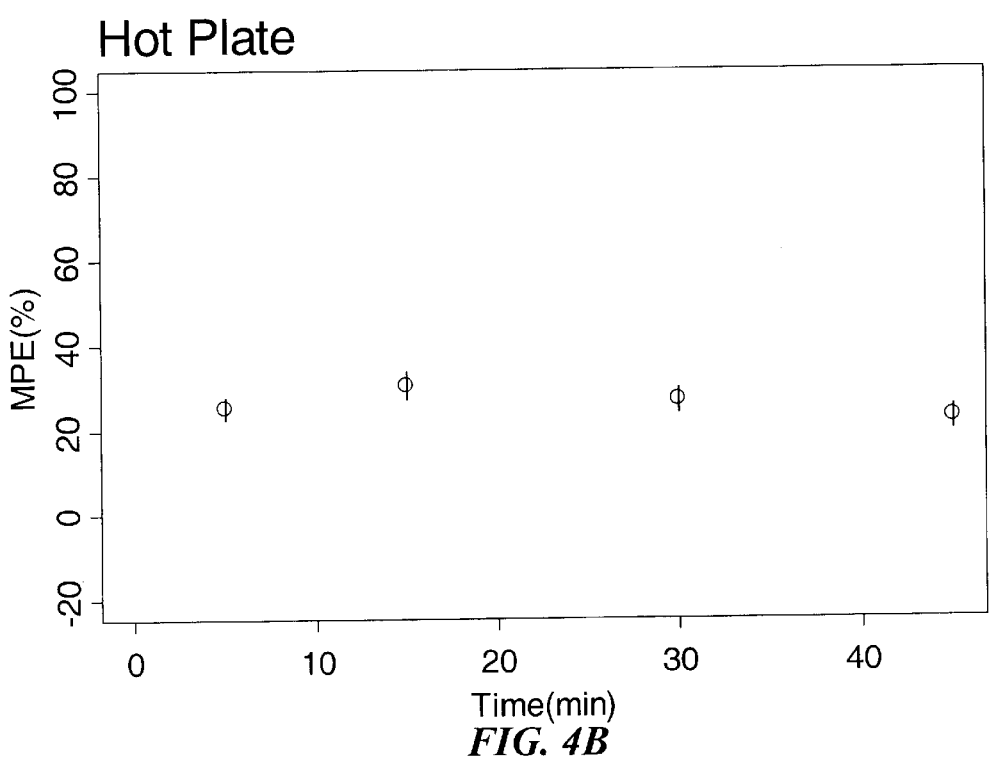
FIG. 4B is a graph of mean and standard error of % MPE at different times for all TCES frequencies in the Hot Plate test.
Figure 4C:
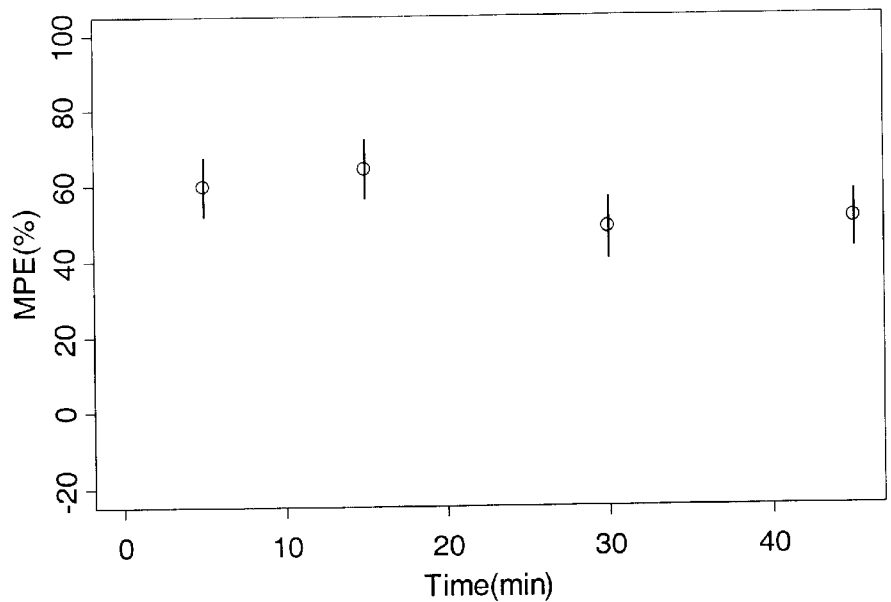
FIG. 4C is a graph of mean and standard error of % MPE at different times for 60 Hz TCES in the Tail Flick Latency test.
Figure 4D:
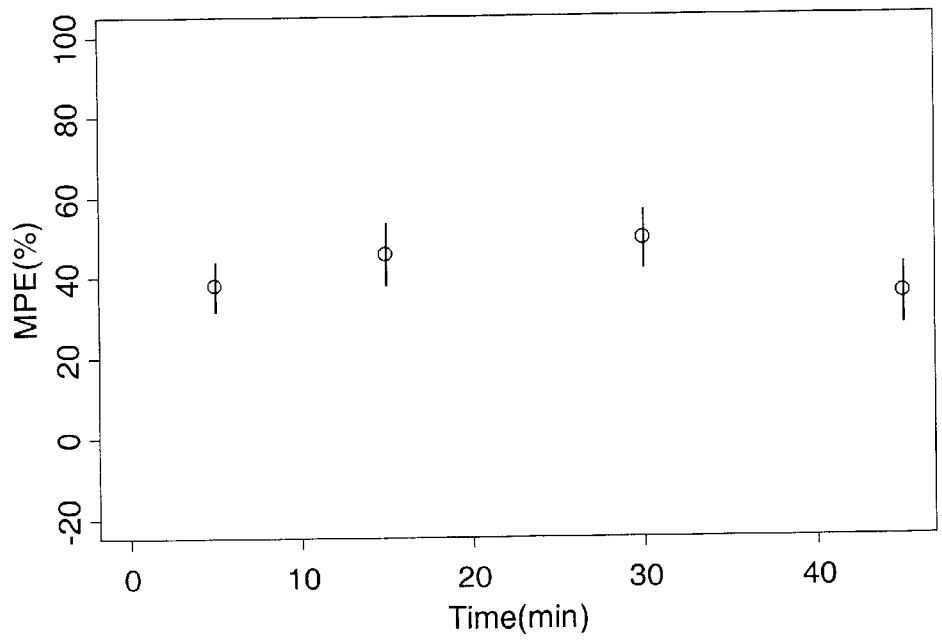
FIG. 4D is a graph of mean and standard error of % MPE at different times for 60 Hz TCES in the Hot Plate test.

FIGS. 4A–4D are graphs of observed effect in % MPE for a time course of TCES application. Open circles are mean values at each time point, and vertical lines are standard errors. FIGS. 4A and 4B show % MPE for all frequencies combined, for TFL and HP test, respectively, while FIGS. 4C and 4D show % MPE for 60 Hz frequency only, again for TFL and HP test, respectively. The effect is substantially equivalent at all time points, illustrating that the analgesic effect of TCES is immediate and sustained over the 45-minute study in a typical rat.

Figure 5A:
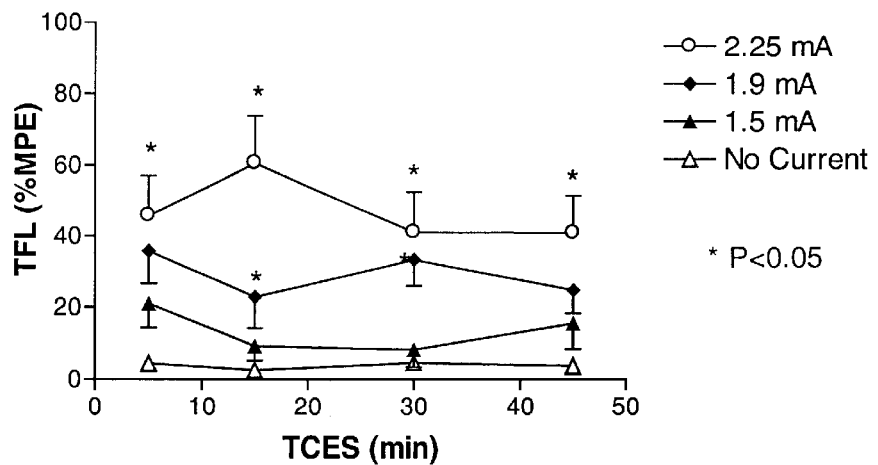
FIG. 5A is a graph of the current dependency of % MPE at 60 Hz TCES in the Tail Flick Latency test.
Figure 5B:
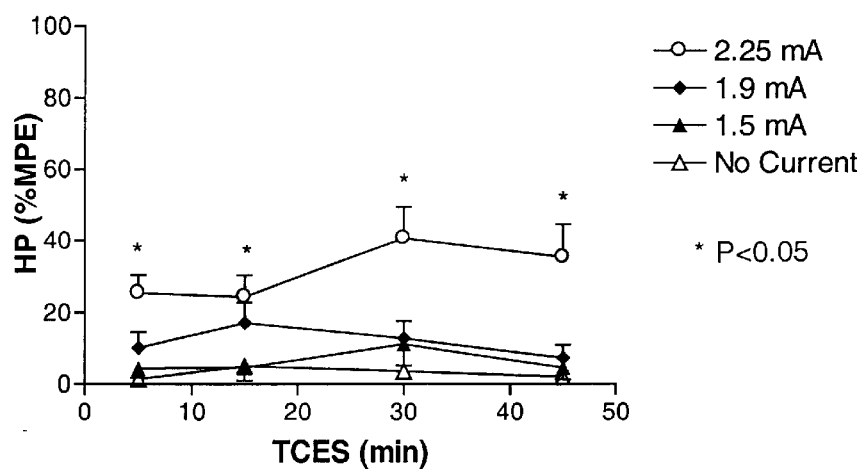
FIG. 5B is a graph of the current dependency of % MPE at 60 Hz TCES in the Hot Plate test.

FIGS. 5A and 5B are graphs of observed effect in % MPE for different values of total current applied for TFL and HP test, respectively. Open circles are mean values, and vertical lines are error bars in one direction only. Asterisks represent P<0.05. All data are at a frequency of 60 Hz. The plots demonstrate that the analgesic effect of TCES is also current dependent, and that the exposure of rats to the same experimental conditions without administration of TCES ("No Current" control group) does not prolong the tail flick or hot plate latencies. Data were analyzed by ANOVA, and then Dunnett's test. P<0.05 was considered statistically significant.

Figure 6A:
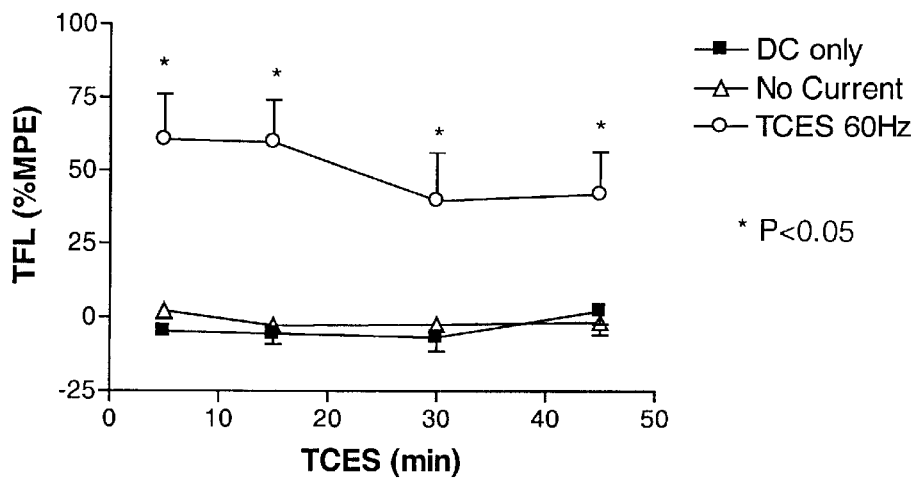
FIGS. 6A–6D are graphs of % MPE versus time, comparing TCES application at 60 Hz with a variety of controls in the Tail Flick Latency and Hot Plate tests.
Figure 6B:
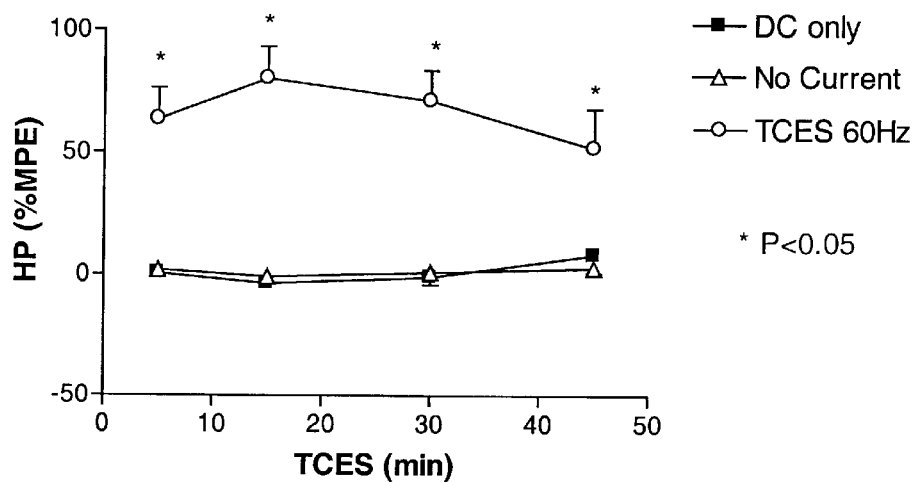
Figure 6C:
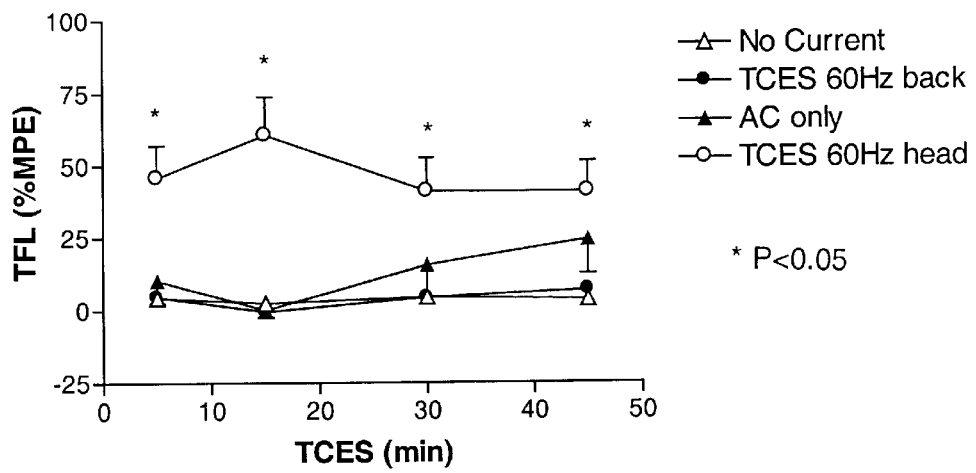
Figure 6D:
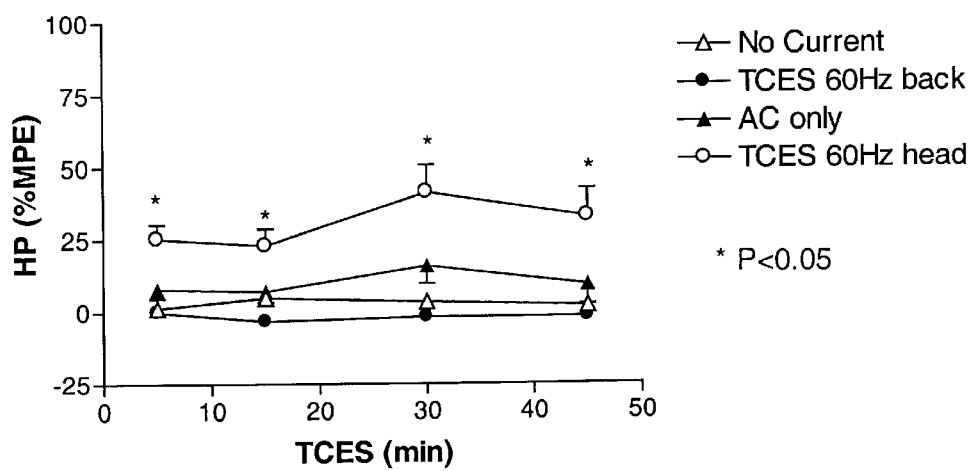

FIGS. 6A–6D are graphs illustrating the observed effect in % MPE for three different controls: DC current alone, AC current alone, and current application to the rat's back. Data were analyzed by ANOVA, and then Dunnett's test. P<0.05 was considered statistically significant. The four graphs document that only administration of a combination of DC and AC produces a statistically significant analgesic effect. Of a special note, as highlighted in FIGS. 6C and 6D, AC current by itself did not provide a statistically significant analgesic effect, contrary to the prior art of Lebedev (1998). As stated above, however, AC current alone might be useful in humans to avoid DC skin bums. FIGS. 6C and 6D also emphasize that electrode placement on the back of the rat does not provide an analgesic effect, signifying that the elicited analgesic effect is site(head)-specific.

Studies have indicated that the current effect of TCES might be mediated by activation of peripheral cutaneous nerves on the subject's head at the sites adjacent to the electrodes. Application of TCES to monkeys [Kano, 1974] showed that when either a local anesthetic was applied under the electrodes or the peripheral nerves were cut, the analgesic effect of TCES disappeared completely. This study indicates that the direct passage of current through the brain might not be responsible for the elicited analgesia. Little attention has been paid to this study, and parameters derived from animal studies utilizing current application through subcutaneous needles, or electrodes affixed to the animal's cranium, continue to be extrapolated for use in humans in clinical practice. It is possible that the analgesic effect observed during subcutaneous current application in experiments is mechanistically different from the effect occurring during cutaneous application, in which mediation by peripheral nerves may be the dominant effect. If, in fact, clinically observed effects of TCES are indeed caused by peripheral nerve activation, then parameters derived from prior experiments may be invalid.

Figure 7:
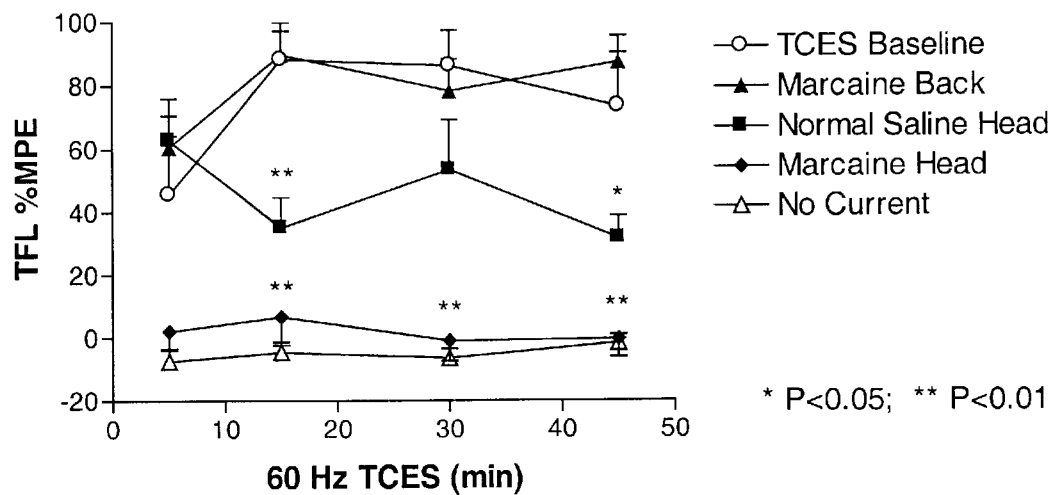
FIG. 7 is a graph of the effect of Marcaine injected under electrode sites on % MPE at 60 Hz TCES in the Tail Flick Latency test.

In order to study the influence of peripheral nerve activation on the analgesic effect, additional experiments were performed with a local anesthetic injected intracutaneously below electrode sites on the head. TCES was applied at 60 Hz under the following conditions: 0.03 ml of 0.5% Marcaine (generic name bupivacaine) injected under each of the three electrode sites on the head; 0.03 ml of 0.5% Marcaine (bupivacaine) injected under three sites on the back; and 0.03 ml of normal saline injected intracutaneously under each of the three electrode sites on the head. The observed effect of 60 Hz TCES under the various conditions is shown in FIG. 7. As demonstrated in the graph, Marcaine injection in the skin of the head was the only condition that showed a substantial reduction in analgesia, as measured by TFL. Data were analyzed by ANOVA, and then Dunnett's test. P<0.05 was considered statistically significant.

The involvement of the cutaneous nerves of the rat's cranium in a TCES analgesic effect was further investigated by application of different conventional TENS (Transcutaneous Electrical Nerve Stimulation) stimulating parameters at the electrode sites used for TCES, and by comparing the elicited analgesic effect to that of TCES. TENS is not FDA approved for use on the head in humans, and in clinical practice it is usually applied as close to the region of the body that produces pain as possible. It is generally agreed that the mechanism by which TENS exerts its analgesic action involves activation of special nerve fibers (the A fibers, or myelinated fibers) inside a peripheral (cutaneous) nerve. This activation blocks pain transmission ("closes the gate") through another type of specialized fibers which are responsible for pain transmission (the C fibers, or unmyelinated fibers) and which are located inside the same peripheral nerve.

Figure 8A:
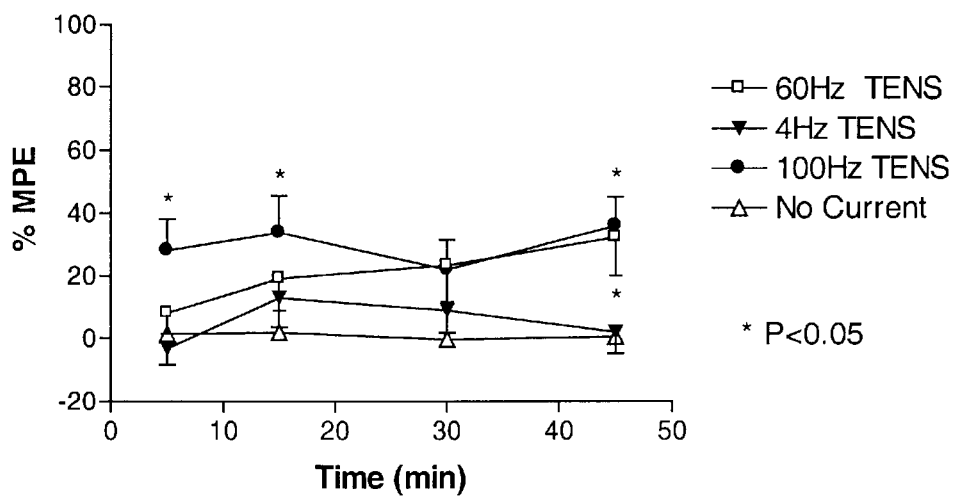
FIG. 8A is a graph of % MPE at different TENS stimulation parameters in the Tail Flick Latency test.
Figure 8B:
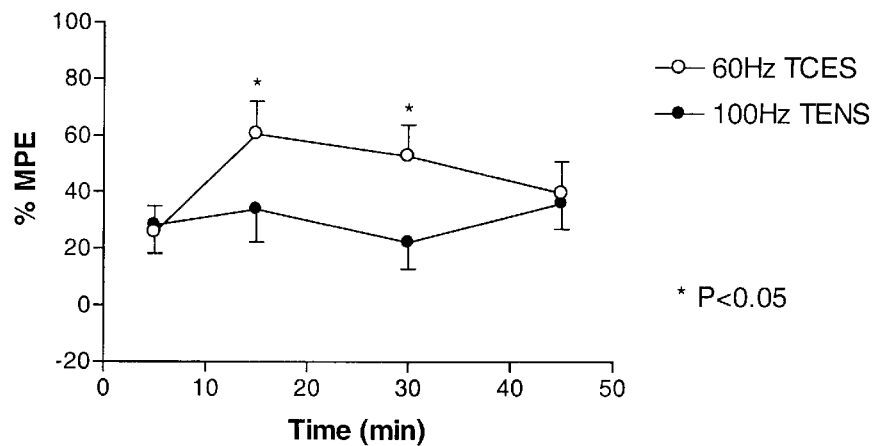
FIG. 8B is a graph comparing % MPE analgesic effect of 60 Hz TCES and 100 Hz TENS in the Tail Flick Latency test.

Rats received either conventional TENS at 4, 60, or 100 Hz or TCES in a random fashion. Data were analyzed by ANOVA and then Dunnett's test. P<0.05 was considered statistically significant. Results are shown in FIG. 8A for different TENS parameters and in FIG. 8B for 100 Hz TENS and 60 Hz TCES. As seen in FIG. 8A, 100 Hz TENS indeed proved to be analgesic. However, the analgesic effect was more significant with TCES (FIG. 8B); data were analyzed by paired T-test.

Marcaine and TENS data strongly indicate that the clinically observed analgesic effects of TCES may indeed be mediated by activation of the peripheral nerves of the cranium. The presented data indicates that the frequencies provided by the present invention are not simple optimizations of existing TCES parameters. Rather, they point to the fact that the mechanism responsible for eliciting analgesia during cutaneous stimulation may be different from that in effect during subcutaneous application. All previous rat experiments used subcutaneous or cranial (bone) application, and therefore likely demonstrated the effect of a different mechanism [Mantz, 1992]. In addition, in Lebedev's original experiments, TFL responses were not studied [Lebedev, 1988].

Figure 9:
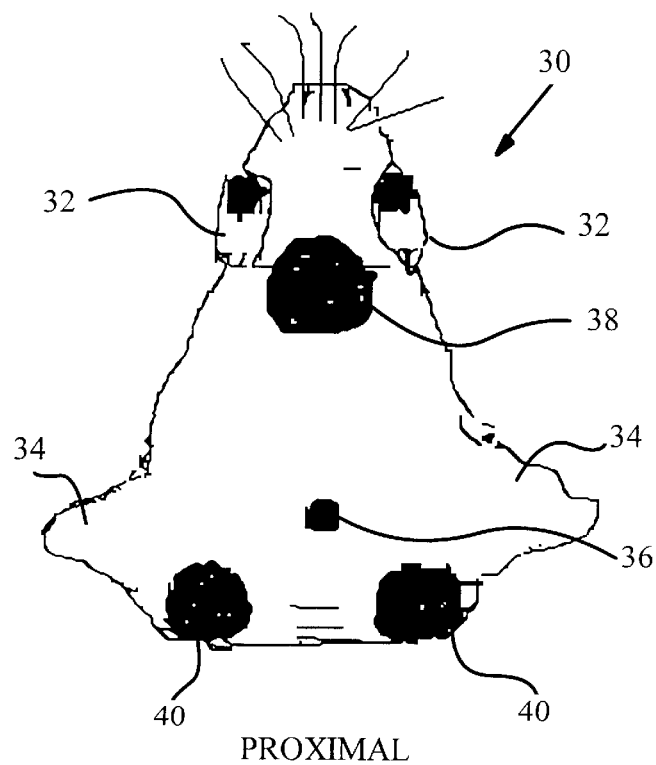
FIG. 9 is a schematic diagram of a rat's head with electrodes placed according to a method of the invention.

The present invention also provides a novel method for cutaneous application of electrodes on rats. FIG. 9 illustrates electrode placement on a rat's head 30. FIG. 9 is a top plan view of head 30, with eyes 32 and ears 34. Also shown is a skull protuberance 36 used to guide electrode placement. A thorough review of rat skull anatomy was necessary to determine locations on the rat's head equivalent to locations used on humans in clinical practice. Anatomical "landmarks" were located on the posterior-lateral surface of the rat skull. These landmarks can be felt through the skin and are used to guide electrode placement. In particular, flat plateau-like regions, roughly located at the posterior-medial region of ears 34, correspond to the location of the mastoid processes. Paired posterior electrodes 40 are therefore placed at these landmarks on the posterior-medial part of ears 34, directly in front of the back of the skull, to mimic human placement at the level of the mastoid processes. Frontal electrode 38 is placed on the midline of head 30, immediately proximal to (behind) an imaginary line connecting the proximal sides of rat eyes 32. This corresponds to the distal pole of the frontal lobes.

Placement of electrodes preferably follows a particular protocol. Preferably, head 30 is shaved, or hair is clipped, before electrode placement. The skin is carefully cleaned to remove oil and other contaminants before the electrodes are placed in the locations described above. Any suitable electrodes 38 and 40 may be used for current application. However, silver-silver chloride electrodes manufactured by In Vivo Metric of Healdsburg, Calif., are preferred, because they are smaller than most commercially-available electrodes. Electrodes 38 and 40 preferably contain a flat plastic surface, which is applied directly to the skin. The plastic surface has a small opening (approximately 4 mm) containing a recessed electrode. A commercially available conductive gel is placed inside the recessed area to allow for current flow between the recessed electrode and skin. Electrodes are attached to the skin by an industrial adhesive. Black Max Gel, manufactured by LOCTITE, is a preferred adhesive. Paired retromastoid electrodes 40 are preferably "double-rim" electrodes, which contain grooves in which an additional amount of adhesive is placed for optimal electrode stabilization. In order to prevent the rats from pulling the electrodes off, and to keep retromastoid electrodes 40 in position, a small skin fold may be used to help secure each of electrodes 40.

The method of electrode placement may be applied to other animal models (e.g., mice) by determining the correct locations for electrode placement. Such applications are within the scope of the present invention.

In addition to the primary application of general anesthesia, the present invention may be used for many other applications. Because of the dramatically larger analgesic effects produced in rat experiments, as compared with prior art TCES methods, the present invention may produce effects that were either not seen previously, or not produced in large enough effects to be worth treating. In addition, the present invention suggests a method of counteracting a tolerance phenomenon frequently observed with TCES by varying the frequency within a predetermined range during current application. For example, the present invention may be used to provide more effective dental analgesia than is produced with current TCES parameters. It is known that TCES can be used to treat chronic pain syndrome and-addiction, especially opiate withdrawal, and the present invention includes novel conditions that should increase the efficacy of these treatments. In addition, pilot human volunteer studies performed by the present inventor using the present invention have shown increased concentration and ability to perform tasks, indicating that the method may be used as treatment for Attention Deficit Disorder (ADD). Other advantages produced by the present invention may include elevated mood and stimulated immune system. It may also be used to treat anxiety disorders, stress, different modes of depression, and post-traumatic stress disorders. Other potential applications include treatment of Parkinson's disease, Alzheimer's disease, neurological dysfunction, appetite disturbance, and sexual dysfunction. Because these conditions are affected by neurotransmitter production levels, they are therefore also likely to be affected by TCES.

The present invention may also be used in combination with analgesic or other drugs to increase the efficacy of the drugs or to decrease the required dosage.

It will be clear to one skilled in the art that the above embodiment may be altered in many ways without departing from the scope of the invention. Accordingly, the scope of the invention should be determined by the following claims and their legal equivalents.

SELECTED REFERENCES

Airapetov L N, Glushenko T S, Taranova N P, Sinitsin L N: Topography of brain regions involved in binding of endogenous opioid peptides released under the influence of transcranial electroanalgesia, in: New Method of Transcranial Electroanalgesia, Abstracts of Scientific Conference, 14–15, Leningrad, 1987.

Akimov G A, Volkov A K: Experience in using transcranial electrical stimulation for treatment of some of the diseases of the nervous system, In: New Method of Transcranial Electroanalgesia, Abstracts of Scientific Conference, 35–36, Leningrad, 1987.

Alling F A, Johnson B D, Elmoghazy E: Cranial electrostimulation (CES) use in the detoxification of opiate-dependent patients, *Journal of Substance Abuse Treatment*, 7: 173–180, 1990.

Auriacombe M, Tignol J, Le Moal M, Stinus L: Transcutaneous electrical stimulation with Limoge current potentiates morphine analgesia and attenuates opiate abstinence syndrome, *Biological Psychiatry*, 15,28(8):650–656, 1990.

Dougherty P M, Dafny N: Transcranial electrostimulation attenuates the severity of naloxone-precipitated morphine withdrawal in rats, *Life Sciences*, 44:2051–2056, 1989.

Fang F, Guo T Z, Davies M F, Maze M: Opioid receptors in the periaqueductal gray mediate analgesic effect of nitrous oxide in rats, *Eur. J. Pharmacol.*, 336(2–3): 137–141, 1997.

Grumbach L: The prediction of analgesic activity in man by animal testing. In: Knighton R S, Dumke P R (eds.), Pain, Little, Brown, Boston, 163–182, 1966.

Guo T Z, Poree L, Golden W, Fujinaga M, Maze M: The antinociceptive response to nitrous oxide is mediated by supraspinal opiate and spinal alpha-2 adrenergic receptors in the rat, *Anesthesiology*, 85(4):846–852, 1996.

Gurchin F A, Kirsanova G V: The use of transcranial electroanalgesia for treatment of pain syndromes of different etiology, In: New Method of Transcranial Electroanalgesia, Abstracts of Scientific conference, 36–37, Leningrad, 1987.

Kano T, Cowan G S, Smith R H: The role of the somatosensory system in general electroanesthesia, *Anesth. Analg.*, 53(5):667–671, 1974.

Kasimova M D, Markov N V, Alieva Z, Mamedova D: Experience with using a new method of electroanalgesia for treatment of acute and chronic eye pains, In: New Method of Transcranial Electroanalgesia, Abstracts of Scientific Conference, 41–42, Leningrad, 1987.

Kartovkin K K, Goncharova E S, Baranovsky A P: Transcranial electroanalgesia as a method of prophylaxis of hypoxic brain damage in pediatric practice, In: New Method of Transcranial Electroanalgesia, Abstracts of Scientific Conference, 23–24, Leningrad, 1987.

Katsnelson IaS, Leosko V A: Evaluation of efficacy of new method of transcranial electroanalgesia in clinical anesthesiology, In: New Method of Transcranial Electroanalgesia, Abstracts of Scientific Conference, 20–22, 1987.

Katsnelson IaS, Leosko V A, Lebedev V P, Khorokhordin N E, Fan A B: Anesthesiologic procedures based on the use of transcranial electric stimulation of the antinociceptive system in surgery of the lungs, *Vestnik Khirurgii Imeni I. I. Grekova*, 143(11):106–107, 1989.

Kovalev MG: Experimental comparison of analgesic effects of a new method of transcranial electrostimulation and Limoge currents, In: New Method of Transcranial Electroanalgesia, Abstracts of Scientific Conference, 11–12, Leningrad, 1987.

Krupitski E M, Burakov A M, Karandashova G F, Katsnelson IaS, Lebedev V P, Grinenko Aja, Borodkin JuS: The administration of transcranial electrical treatment for affective disturbances therapy in alcoholic patients, *Drug and Alcohol Dependence*, 27(1):1–6, 1991.

Lebedev V P, Katsnelson IaS, Leosko V A, Baranovsky A L, Shlemis G I: Anesthesia of laboratory animals achieved with the combined effects of direct and impulse currents, *Fiziol Zh SSSR*, 69(8):1120–1123, 1983.

Lebedev V P, Airapetov L N, Katsnelson IaS, Savchenko A B, Petriaevskaia N V: Activation of antinociceptive system of the brain during transcranial electroanalgesia and the role of opioid and mediating mechanisms in the formation of this effect, In: New Method of Transcranial Electroanalgesia, abstracts of Scientific Conference, 12–14, Leningrad, 1987.

Lebedev V P, Savchenko A B, Petriaevskaia N V: The opiate mechanism of transcranial electroanalgesia in rats and mice, *Fiziol Zh SSSR*, 74(9):1249–1256, 1988.

Lebedev V P: Transcranial Electrostimulation: a new approach. (Experimental and clinical rationale and equipment). In: *Transcranial Electrostimulation*, 26–35, St. Petersburg, Russia, 1998.

Levin R H, McGuire F L: Electrical Anesthesia. Effects of prolonged subconvulsive cerebral electrostimulation on memory, intellectual level, and subjective report of pain, *Anesthesia and Analgesia, Current Researches*, 45(2): 222–225, 1966.

Limoge A: *An Introduction to Electroanesthesia*. Baltimore: University Park Press: 120, 1975.

Limoge A, Robert C, Stanley T: Trancutaneous cranial electrical stimulation (TCES): A review 1998. *Neuroscience and Behavioral Reviews*, 23:529–538, 1999.

Lippold O C J, Redfearn J W T: Mental changes resulting from the passage of small direct currents through the human brain, *Brit. J. Psychiatry*, 110: 768–772, 1964.

Malin D H, Lake J R, Hamilton R F, Skolnick M H: Augmented analgesic effects of enkephalinase inhibitors combined with transcranial electrostimulation, *Life Sciences*, 44:1371–1376, 1989.

Mantz J, Azerad J. Limoge A, Desmonts J M: Transcranial electrical stimulation with Limoge's currents decreases halothane requirements in rats. Evidence for the involvement of endogenous opioids, *Anesthesiology*, 76(2): 253–260, 1992.

Richter W R, Zouhar R L, Tatsuno J, Smith R H, Cullen S C: Electron microscopy of the Macaca mulatta brain after repeated applications of electric current, *Anesthesiology*, 36(4): 374–377, 1972.

Rychkova S V, Aleksandrova V A: Transcranial electrostimulation (the mechanism of its action and its analgesic and associated effects), *Voprosy kurortologii, Fizioterapii I Lechebnoi Fizicheskoi kultury*, November–December, 6:23–27, 1994.

Skorometz A A, Kodzaev Y K, Sorokoumov V A, Sidorov A M: Use of transcranial electroanalgesia for treatment of some neurological pain syndromes, In: New Method of Transcranial Electroanalgesia, Abstracts of Scientific Conference, 34–35, Leningrad, 1987.

Smith R H: Electroanesthesia. Review., *Anesthesiology*: 60–72, January, 1971.

Stanley T H, Gazalaa J A, Limoge A, Louville Y: Transcutaneous cranial electrical stimulation increases the potency of nitrous oxide in humans, *Anesthesiology*, 57:293–297, 1982A.

Stanley T H, Gazalaa J A, Atinault A, Coeytaux R, Limoge A, Louville Y: Transcutaneous cranial electrical stimulation decreases narcotic requirements during neuroleptanesthesia and operation in man, *Anesth Analg*, 61:863–866, 1982B.

Stinus L, Auriacombe M, Tignol J, Limoge A, Le Moal: Transcranial electrical stimulation with high frequency intermittent current (Limoge's) potentiates opiate-induced analgesia: blind studies, *Pain*, 42: 351–363, 1990.

Vanevsky V L, Grinchenko S A: Comparison of two methods of electrical stimulation used as part of an anesthetic management during surgery, In; New Method of Transcranial Electroanalgesia, Abstracts of Scientific Conference, 22–23, Leningrad, 1987.

Zamiatnina N M: Investigation of the use of a new method of transcranial electroanalgesia for orthopedic surgery in pediatrics, In: New Method of Transcranial Electroanalgesia, Abstracts of Scientific Conference, 31–32, Leningrad, 1987.

What is claimed is:

1. A method of eliciting analgesia in a human subject, comprising:

a) removably fixing a first electrode and a pair of second electrodes to the skin of said subject's head;

b) supplying electrical current to said first electrode and to said pair of second electrodes, wherein said electrical current comprises rectangular current pulses superimposed on direct current, and wherein said current pulses are supplied at a particular frequency of between approximately 30 Hz and approximately 65 Hz, wherein a total current value supplied is between approximately 0.2 mA and approximately 20 mA, wherein said total current value is a sum of said direct current and a Mean Absolute Deviation (MAD) value of said current pulses; and c) periodically changing said particular frequency to a different frequency.

2. The method of claim 1 wherein the method is used as part of anesthesia management during surgery.

3. The method of claim 1 wherein the method is used during a post-operative period.

4. The method of claim 1 wherein said current pulses are supplied at a frequency of between approximately 40 Hz and approximately 60 Hz.

5. The method of claim 4 wherein said current pulses are supplied at a frequency of approximately 60 Hz.

6. The method of claim 1 wherein said different frequency is between approximately 30 Hz and approximately 65 Hz.

7. The method of claim 6 wherein said particular frequency is changed to said different frequency at intervals of between approximately 5 minutes and approximately 60 minutes.

8. The method of claim 1 wherein said different frequency is between approximately 10 Hz and approximately 100 Hz.

9. The method of claim 8 wherein said particular frequency is changed to said different frequency at intervals of between approximately 15 minutes and approximately 60 minutes.

10. The method of claim 1 wherein said particular frequency is selected in dependence on said human subject.

11. The method of claim 1 wherein said total current supplied is between approximately 2 mA and approximately 10 mA.

12. The method of claim 1 wherein a ratio between the value of said direct current and said Mean Absolute Deviation (MAD) value of said current pulses is between approximately 5:1 and approximately 1:1.

13. The method of claim 12 wherein said ratio is approximately 2:1.

14. The method of claim 1 wherein a duration of each current pulse is below approximately 8 msec.

15. The method of claim 14 wherein said duration is approximately equal to 3.5 msec.

16. The method of claim 1 further comprising changing a polarity of said electrical current at regular intervals.

17. The method of claim 16 wherein said regular intervals are between approximately 5 minutes and approximately 15 minutes.

18. The method of claim 1 wherein each of said rectangular current pulses is substituted with bursts of high frequency pulses wherein said bursts of high frequency pulses appear with a period of between approximately 30 Hz and approximately 65 Hz, and wherein each of said high frequency pulses is between approximately 10 kHz and approximately 10 MHz.

19. A method of transcranial electrical stimulation, comprising:
   a) removably fixing a first electrode and a pair of second electrodes to the skin of said subject's head;
   b) supplying electrical current to said first electrode and to said pair of second electrodes, wherein said electrical current comprises rectangular current pulses superimposed on direct current, and wherein said current pulses are supplied at a particular frequency of between approximately 30 Hz and approximately 65 Hz, wherein a total current value supplied is between approximately 0.2 mA and approximately 20 mA, wherein said total current value is a sum of said direct current and a Mean Absolute Deviation (MAD) value of said current pulses; and
   c) periodically changing said particular frequency to a different frequency.

20. A method of treating a medical condition in a human subject, comprising:
   a) removably fixing a first electrode and a pair of second electrodes to the skin of said subject's head;
   b) supplying electrical current to said first electrode and to said pair of second electrodes, wherein said electrical current comprises rectangular current pulses superimposed on direct current, and wherein said current pulses are supplied at a particular frequency of between approximately 30 Hz and approximately 65 Hz, wherein a total current value supplied is between approximately 0.2 mA and approximately 20 mA, wherein said total current value is a sum of said direct current and a Mean Absolute Deviation (MAD) value of said current pulses; and
   c) periodically changing said particular frequency to a different frequency;
wherein said medical condition is selected from the group consisting of acute and chronic pain syndrome, immune system depression, and decreased wound healing.

21. The method of claim 20 wherein the method is used during a post-operative period.

22. A method of treating a medical condition in a human subject, comprising:
   a) removably fixing a first electrode and a pair of second electrodes to the skin of said subject's head;
   b) supplying electrical current to said first electrode and to said pair of second electrodes, wherein said electrical current comprises rectangular current pulses superimposed on direct current, and wherein said current pulses are supplied at a particular frequency of between approximately 30 Hz and approximately 65 Hz, wherein a total current value supplied is between approximately 0.2 mA and approximately 20 mA, wherein said total current value is a sum of said direct current and a Mean Absolute Deviation (MAD) value of said current pulses; and
   c) periodically changing said particular frequency to a different frequency;
wherein said medical condition is selected from the group consisting of alcohol withdrawal, opiate withdrawal, Attention Deficit Disorder, anxiety, depression, mood disturbance, Post-Traumatic Stress Disorder, appetite disturbance, sexual dysfunction, Parkinson's disease, Alzheimer's disease, and neurological dysfunction.

23. A method of producing a desired effect in a human subject, comprising:
   a) removably fixing a first electrode and a pair of second electrodes to the skin of said subject's head;
   b) supplying electrical current to said first electrode and to said pair of second electrodes, wherein said electrical current comprises rectangular current pulses superimposed on direct current, and wherein said current pulses are supplied at a particular frequency of between approximately 30 Hz and approximately 65 Hz, wherein a total current value supplied is between approximately 0.2 mA and approximately 20 mA, wherein said total current value is a sum of said direct current and a Mean Absolute Deviation (MAD) value of said current pulses; and
   c) periodically changing said particular frequency to a different frequency;
wherein said desired effect is selected from the group consisting of elevated mood, increased attention, and stimulated immune system.

* * * * *